Figure 1:
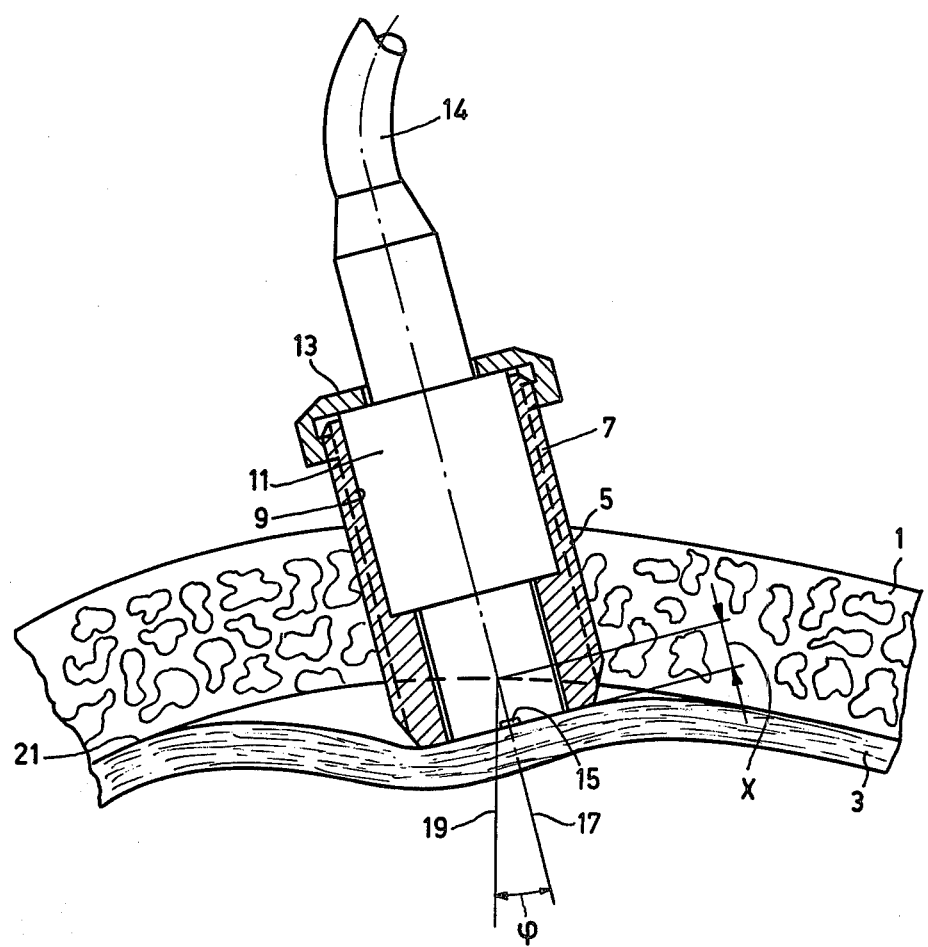

United States Patent [19]

van Lotringen

[11] 4,186,728
[45] Feb. 5, 1980

[54] APPARATUS FOR ADAPTING A SKULL FOR THE APPLICATION OF A PRESSURE TRANSDUCER

[75] Inventor: Antonius L. M. van Lotringen, Eindhoven, Netherlands

[73] Assignee: U.S. Philips Corporation, New York, N.Y.

[21] Appl. No.: 859,744

[22] Filed: Dec. 12, 1977

[30] Foreign Application Priority Data

Feb. 18, 1977 [NL] Netherlands .................... 7701722

[51] Int. Cl.² .................................................. A61B 19/00
[52] U.S. Cl. .................................. 128/1 R; 128/748; 128/303 R
[58] Field of Search ................... 3/9.1, 9.9, 13; 128/1 R, 2 R, 2.05 E, 92 E, 92 EB, 92 EC, 215, 221, 303 R, 303 B, 305, 305.1, 310, 347, 348, 2 N

[56] References Cited

U.S. PATENT DOCUMENTS 3,815,577   6/1974   Bucalo ............................ 128/1 R

FOREIGN PATENT DOCUMENTS 2621909   1/1977   Fed. Rep. of Germany .......... 128/2 R
985553    7/1951   France ............................ 128/2.05 E
296559    4/1971   U.S.S.R. .......................... 128/2 R

OTHER PUBLICATIONS

Anon., "Philips Gloeilampenfabrieken Medical Systems Division Publication No. 9822 807 10101" Pub. 11/1976.

Primary Examiner—Clifford D. Crowder
Assistant Examiner—James R. Feyrer
Attorney, Agent, or Firm—Thomas A. Briody; Edward J. Connors, Jr.; Jack E. Haken

[57] ABSTRACT

Means for adapting a skull for the application of a pressure transducer comprising a hollow screw which can be introduced into the skull and which can accommodate the pressure transducer, a tool for introducing the screw, and an indicator for indicating when the screw has been introduced into the skull to a desired depth.

5 Claims, 4 Drawing Figures

U.S. Patent  Feb. 5, 1980  Sheet 2 of 2  4,186,728
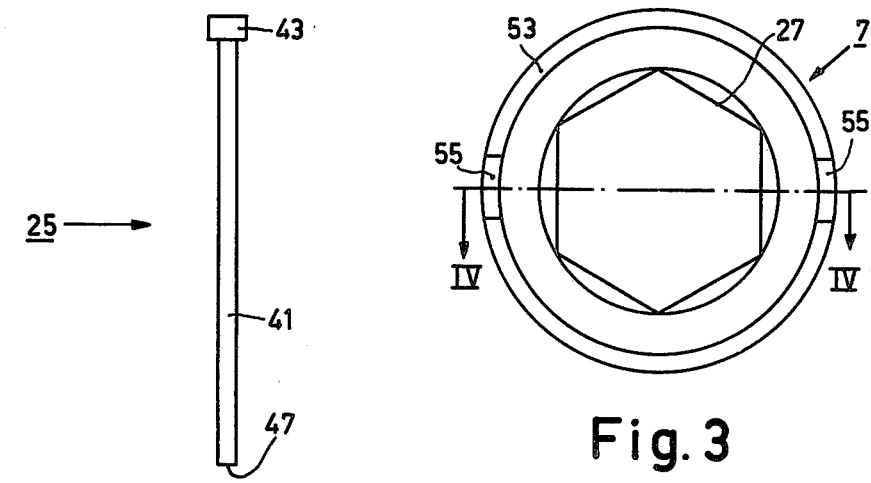
Fig. 3
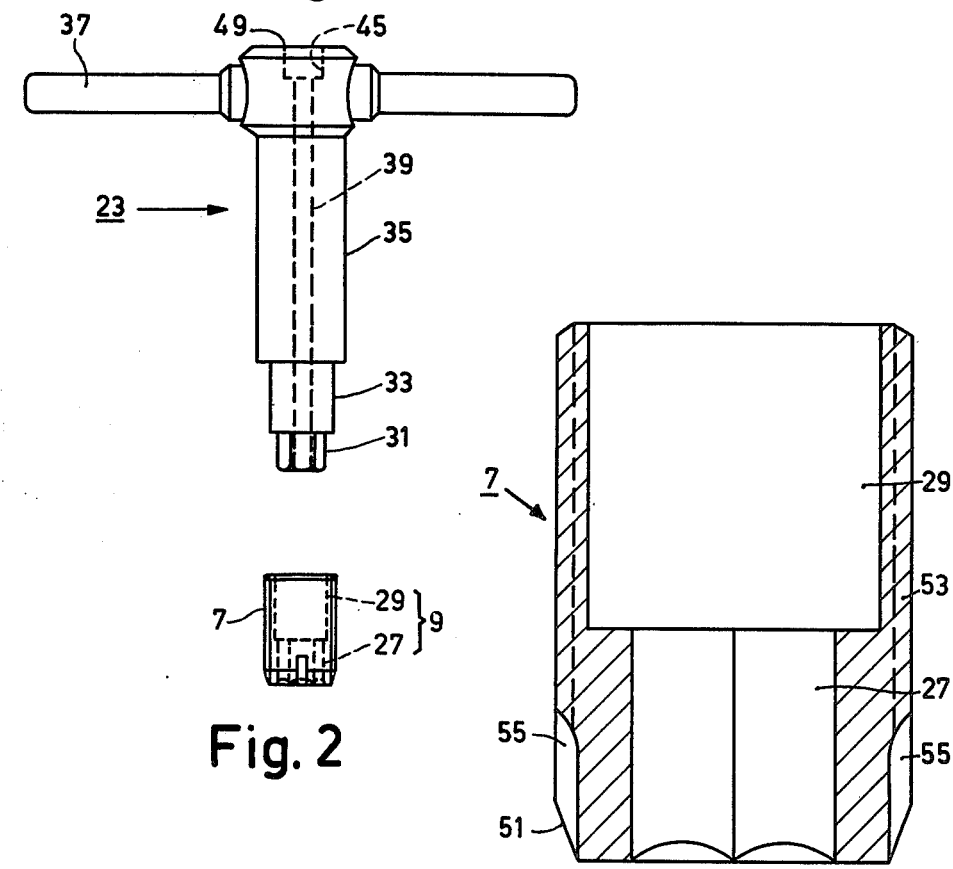
Fig. 2
Fig. 4

APPARATUS FOR ADAPTING A SKULL FOR THE APPLICATION OF A PRESSURE TRANSDUCER

The invention relates to means for adapting a human or animal skull for the application of a pressure transducer for the epidural measurement of the intracranial pressure, comprising a scew with a continuous axial cavity in which the pressure transducer can be accommodated, and a tool which is adapted to co-operate with the screw for introducing said screw into a hole which has been drilled into the skull. Publication No. 9822 807 10101, by N. V. Philips' Gloeilampenfabrieken, Medical Systems Division of Eindhoven, The Netherlands, entitled "Intra Cranial Pressure", published in November 1976, describes how a skull can be adapted for the temporary application of a pressure transducer. For this purpose a hollow screw is fitted into the skull, the cavity of said screw putting the dura mater into communication with the atmosphere. In this screw a pressure transducer is fitted which contains a flat measuring element. Application must be effected so that the measuring element engages with the dura mater without significantly deforming it. Only when this requirement is met, it is ensured that the measuring element exclusively responds to the intracranial pressure. When the measuring element is positioned obliquely or is disposed to deep, measuring errors are produced due to forces exerted by the dura mater itself on the measuring element and which are superimposed on the forces exerted on the measuring element as a result of the intra cranial pressure via the dura mater. In practice it has been found that the best results are obtained when the screw is introduced into the skull so far that the dura mater is depressed by approx 1 mm, while the angle between the axis of the cavity in the screw and the normal to the bounding surface between skull wall and dura mater is minimal and on no account exceeds 10°.

The penetration depth of the known screw is determined by fitting rings between a collar formed on the screw and the skull wall. These rings also serve as a seal in order to prevent loss of fluid. It has been found that this method of defining the penetration depth does not always guarantee that the screw has actually been introduced into the skull down to the correct depth. It is an object of the invention to provide means of the type mentioned in the preamble, which do guarantee this.

According to the invention the means are therefore characterized in that an indicator is provided, which is adapted to indicate when the screw has been introduced into the skull down to the desired depth, which indicator comprises a sensor which in the operating condition extends through the cavity in the screw.

Since the depth is now indicated when the screw is introduced, it is assured that always exactly the correct depth is attained. A preferred embodiment of the device in accordance with the invention, which comprises simple components which can therefore readily be sterilized, is characterized in that the tool has a continuous cavity whose axis in the operating condition substantially coincides with the axis of the cavity in the screw, and that the sensor is constituted by an axially movable pin which extends through both cavities, which pin has a first mark which upon reaching a specific depth coincides with a second mark provided on the tool.

The invention will now be described in more detail with reference to the drawing. In the drawing:

FIG. 1 is a schematic representation of a pressure transducer applied to a skull, FIG. 2 is an exploded view of an embodiment of the means in accordance with the invention, FIG. 3 is a bottom view on an enlarged scale of a screw belonging to the means shown in FIG. 2, and FIG. 4 is a cross-section taken on the line IV—IV in FIG. 3.

FIG. 1 schematically shows a part of a skull wall 1 with the dura mater 3 underneath it. In the skull wall 1 a hole 5 has been drilled, in which a self-tapping screw 7 is introduced. In the screw 7 an axially extending cavity 9 is formed, in which a pressure transducer 11 is disposed, which is retained by a coupling nut 13. A connecting lead 14 connects the pressure transducer 11 to a measuring instrument (not shown). At the lower end of the pressure transducer 11 a flat measuring element 15 (for example consisting of a silicon wafer in which strain gauges are formed) is located, which engages with the dura mater 3. In this way the pressure inside the skull can be measured through the dura mater (epidural measurement of the intracranial pressure). This method of pressure measurement involves comparatively little risk and discomfort to the patient and has the required accuracy.

In the ideal case the plane of the measuring element 15 is parallel to the inner surface 21 of the skull. The measuring element 15 should be disposed at a depth X of approximately 1 mm below said inner surface. In practice, it is found that an angle $\phi$ between the normals 17 and 19 of maximum 10° is still tolerable, whilst the depth X may very between approximately 0.3 and 1.3 mm.

FIG. 2 shows an exploded view of the means in accordance with the invention for adapting the skull for the application of the pressure transducer 11. These means comprise the screw 7, a tool 23 which is adapted to cooperate with the screw for introducing the screw into the skull wall 1, and an indicator 25 for indicating when the screw has been introduced into the skull wall 1 to the desired depth.

The cavity 9 (shown dotted) formed in the screw 7 comprises a lower hexagonal portion 27 and an upper circular-cylindrical portion 29 (also see FIGS. 3 and 4.) The lower portion 31 of the tool 23 is also hexagonal, so that it can cooperate with the portion 27 for introducing the screw 7. Above the hexagonal portion 31 the tool has a circular-cylindrical portion 33 whose diameter has been adapted to that of the corresponding portion 29 of the screw 7, so that the axes of the tool and the screw accurately coincide when the tool is inserted into the screw. As a result of this the position of the screw 7 in the skull wall 1 and thus the angle $\phi$ is substantially fully determined by the position of the tool 23 relative to the skull wall. Thus, it is found to be possible without problems and without any further aids to obtain an angle $\phi$ which is substantially smaller than the required 10°.

The tool 23 furthermore has a shank 35 and a handle 37. A cavity 39 (shown dotted) extends through the tool, which cavity is coaxial with the cavity 9 in the screw 7 in the operating condition. The indicator 25 consists of a pin 41 which serves as a sensor, which pin has a head 43 whose top is flat. The cavity 39 in the tool 23 is shaped so that the pin 41 can move in it, in the axial direction, whilst the head 43 cannot reach any further than the upper portion which has been widened to a chamber 45. When the pin 41 is disposed in the cavity 39, the lower end 47 of the pin 41 projects for example 2 mm below the underside of the hexagonal portion 31 and the head 43 is accommodated in the chamber 45. As soon as the dura mater is reached when the screw 7 is introduced, the pin 41 is pushed upwards in the cavity 39. In order to minimize the pressure on the dura mater, the pin 41 is preferably made of a tubular material. When the top of the head 43 is level with the upper edge 49 of the chamber 45, the screw is given one more turn and then the screw 7 is pressed exactly 1 mm into the dura mater. The transducer 11 can then be applied and secured with the coupling nut 13.

In the example described the top of the surface of the head 43 constitutes a first mark which when a specific depth is reached coincides with the top edge 49 of the chamber 45, which constitutes a second mark. It is obvious that, if desired other marks can be provided on the indicator 25 and the tool 23. For example, the head 43 may be prolonged, so that it always projects from the edge 49. The head may then be provided with a scale graduation. It is also possible to mount a sensor at the underside of the tool 23, which upon reaching the dura mater actuates an electrical contact, so that an optical or acoustic signal is given.

FIGS. 3 and 4 on an enlarged scale show the screw 7 in bottom view and in longitudinal section to illustrate some details. In order to facilitate the introduction of the screw 7 into a hole which has been drilled into the skull wall 1 and in which no screw-thread has been tapped, the lower end of the screw is provided with an oblique edge 51 and two slits 55, which extend parallel to the screw axis, are formed in the lower portion of the thread 53. The edges of said slits constitute cutting edges, so that tapping screw-thread into the wall of the hole 5 presents no problems. Obviously the slits 55 interrupt the screw thread 53. It is found to be favourable to minimize the number of interrupted threads, so that as many as possible (at least two) uninterrupted threads are left. This is because it has been found that an uninterrupted thread constitutes an excellent seal against moisture, in conjunction with the bone of the skull wall 1. As a result of this, no separate seals are necessary, as with the known screw. As such rings are neither needed for defining the penetration depth, the screw 7 need not have a collar and rings, which facilitates sterilization. In practice, it has been found that the slit 55 should be approximately 5.5 mm long. The uninterrupted portion of the thread 53 is then introduced into the skull wall 1 over a length of approximately 3 mm, which guarantees adequate sealing.

What is claimed is:

1. Apparatus for adapting a human or animal skull for the application of a pressure transducer for the epidural measurement of the intracranial pressure, comprising: a screw with a continuous axial cavity in which the pressure transducer can be accommodated; a tool which is shaped to engage with the screw for introducing said screw into a hole in the skull; and indicator means which function to indicate when the screw has been introduced into the hole to the desired depth, which indicator means include a sensor which, in the operating condition, extends through the cavity in the screw.

2. Apparatus as claimed in claim 1, wherein the tool (23) has a continuous cavity (39) whose axis in the operating condition substantially coincides with the axis of the cavity (9) in the screw, and the sensor comprises an axially movable pin (41) which extends through the two cavities (39, 9), which pin has a first mark which upon reaching a specific depth coincides with a second mark on the tool (23).

3. Apparatus as claimed in claim 2, characterized in that the first mark comprises an end face of a head (43) which is located at that end of the pin (41) which is remote from the screw (7) and the second mark comprises an edge (49) of the cavity (39) in the tool (23) which is remote from the screw (7).

4. Apparatus as claimed in claim 1 wherein the thread (53) of the screw (7) is uninterrupted over more than two leads.

5. Apparatus as claimed in claim 1, wherein the cavity (9) in the screw (7) comprises a non-round portion (27) disposed near the front-most end, viewed in the direction of the screw, and shaped to fit a correspondingly shaped portion (31) of the tool (23), and wherein the cavity (9) has a wider circular-cylindrical portion, near its other end which is shaped to fit a circular-cylindrical portion (33) of the tool (23) adjoining the non-round portion (31) thereof.

* * * * *